(12) United States Patent
Nuissl et al.

(10) Patent No.: US 8,376,096 B2
(45) Date of Patent: Feb. 19, 2013

(54) ROLLER BEARING HAVING A BRAKE DEVICE

(75) Inventors: Christian Nuissl, Fuerth (DE); Juergen Stoelzle, Erlangen (DE)

(73) Assignee: Schaeffler Technologies AG & Co. KG, Herzogenaurach (DE)

( * ) Notice: Subject to any disclaimer, the term of this patent is extended or adjusted under 35 U.S.C. 154(b) by 334 days.

(21) Appl. No.: 12/739,452

(22) PCT Filed: Sep. 12, 2008

(86) PCT No.: PCT/EP2008/062164
§ 371 (c)(1),
(2), (4) Date: Jun. 3, 2010

(87) PCT Pub. No.: WO2009/053168
PCT Pub. Date: Apr. 30, 2009

(65) Prior Publication Data
US 2012/0020602 A1    Jan. 26, 2012

(30) Foreign Application Priority Data
Oct. 26, 2007  (DE) .................. 10 2007 051 229

(51) Int. Cl.
*B60T 13/04* (2006.01)
*F16C 33/34* (2006.01)
(52) U.S. Cl. ............... 188/171; 188/161; 384/565
(58) Field of Classification Search .......... 188/158, 188/161, 163, 17, 25, 26, 164, 171; 384/548, 384/565, 572
See application file for complete search history.

(56) References Cited

U.S. PATENT DOCUMENTS

| | | | |
|---|---|---|---|
| 3,752,267 A | 8/1973 | Dovell et al. | |
| 5,152,614 A * | 10/1992 | Albert et al. | 384/43 |
| 2005/0282673 A1* | 12/2005 | Knappe et al. | 474/198 |

FOREIGN PATENT DOCUMENTS

| | | |
|---|---|---|
| DE | 19 04 954 | 6/1970 |
| DE | 37 25 972 | 2/1989 |
| DE | 41 04 137 | 8/1992 |
| DE | 100 07 317 A | 9/2000 |
| DE | 100 07 317 A1 | 9/2000 |
| DE | 101 27 487 A | 12/2002 |
| DE | 101 27 487 A1 | 12/2002 |
| JP | 62020923 A * | 1/1987 |

* cited by examiner

*Primary Examiner* — Thomas J Williams
(74) *Attorney, Agent, or Firm* — Lucas & Mercanti, LLP; Klaus P. Stoffel

(57) ABSTRACT

A roller bearing, which has a brake device made of outer and inner bearing rings, between which rollers roll on corresponding rings, a displaceable braking element connected to one of the bearing rings pressed against an associated opposite surface connected to the other bearing ring to generate a braking effect due to a frictional fit, which can be neutralized by an electromagnet. The electromagnet is made of one of the hearing rings as a soft iron core, and a coil encompassing the ring. A ferromagnetic armature plate is connected to one of the bearing rings and is pressed towards a pressure plate, which is connected to the other bearing ring. At least one disc is disposed between the armature plate and pressure plate. The disc is operationally connected to brake linings on both sides, and each have a form-fit connection to one of the bearing rings by guide pins.

11 Claims, 4 Drawing Sheets

US 8,376,096 B2

ROLLER BEARING HAVING A BRAKE DEVICE

This application is a 371 of PCT/EP2008/062164 filed Sep. 12, 2008, which in turn claims the priority of DE 10 2007051 229.7 filed Oct. 26, 2007, the priority of both applications is hereby claimed and both applications are incorporated by reference herein.

FIELD OF THE INVENTION

The invention relates to a rolling bearing having a braking device, in particular a rotational connection, comprising an outer bearing ring and an inner bearing ring, between which rolling bodies are in rolling motion on associated raceways, wherein in order to produce a braking effect by frictional engagement a displaceable braking element connected to one of the bearing rings is pressed against an opposing face connected to the associated other bearing ring and the frictional engagement may be canceled by means of an electromagnet.

BACKGROUND OF THE INVENTION

Rolling bearings having braking devices have long been known. There is a risk with rolling bearing rotational connections on wind power stations, for example, that they will fail after a relatively short time due to furrowing in the raceways. This phenomenon is produced due, in particular, to slight pivot movements in order to compensate for the wind direction, during which the rolling bodies slide on the raceway. In order to preclude this wear, various measures are known for increasing the low rotational resistance in rolling bearings. DE 37 25 972 A1 and DE 41 04 137 A1 in this context propose to use an additionally rotating braking device. The braking force and hence the desired rotational resistance can then be adjusted from the outside. The disadvantage to this in the first case is that the braking element can be cancelled only when the wind power station is shut down. In the second case the braking device comprises many mechanical components, making it complex to manufacture and complicated to handle.

DE 19 04 954 B discloses a pivotless rotational connection for excavators, cranes or the like for supporting a swiveling superstructure on a substructure. This rotational connection in each case comprises a one-part swivel ring and a further, two-part swivel ring assembled from two profile rings. The two swivel rings are each braced against one another by the balls of a double-row ball bearing and are equipped with a braking device. The braking devices each have one or more brake shoe carriers, which are attached to a component connected to the one-part swivel ring. A disadvantage with this arrangement is that the braking devices are located outside the actual bearing arrangement and therefore take up additional overall space.

A bearing arrangement of generic type with braking function has been previously disclosed by DE 101 27 487 A1. The radial bearing arrangement according to FIG. 1 has a deep-groove ball bearing embodied as a radial bearing and a braking device located axially next to this. The deep-groove ball bearing comprises the inner ring, the outer ring and bearing balls arranged in a cage between them. The deep-groove ball bearing furthermore comprises two sealing rings, which seal the annular space from the surroundings on both sides. The braking device has an inner retaining ring and an outer retaining ring. Fixed to a radially outward-facing flange of the inner retaining ring by way of a flat wire spring is a brake disk, which is composed of a ferromagnetic material and has a brake lining on its side remote from the flange. The brake disk is rotationally locked to the inner retaining ring via the flat wire spring mounting and is displaceable in an axial direction. Opposite the brake lining an opposing face, against which the brake lining is pressed during braking, is formed on the outer retaining ring. The outer retaining ring furthermore has an electrical coil and one or more permanent magnets, which are each arranged in the area between the brake disk and the deep-groove ball bearing and are mechanically connected to the outer retaining ring and consequently also to the opposing face.

A disadvantage to this is that the braking device has to be flanged onto the bearing in an axial direction as an external component and therefore takes up additional overall space. The retaining rings are of relatively complicated construction and have first to be connected in a complex process by pins to the bearing rings. A further disadvantage is that the braking effect is initiated by a permanent magnet, which attracts the brake disk. In certain applications, however, a constant magnetic field is detrimental, since iron-containing dirt is sometimes attracted by the bearing. Moreover, it is disadvantageous in the braking devices described in the preceding text that they develop too low a braking force for certain applications.

SUMMARY OF THE INVENTION

The object of the invention, therefore, is to avoid the aforementioned disadvantages and to provide a braking device, which is easy to manufacture and which develops high braking performance in a minimum amount of installation space.

According to the invention this object is achieved in that the electromagnet comprises one of the bearing rings as soft-iron core and a coil surrounding the latter, in that a ferromagnetic armature plate which is connected to one of the bearing rings is pressed in the direction of a pressure plate which is connected to the other bearing ring, and in each case at least one disk is arranged between the armature plate and the pressure plate, which disks are operatively connected on both sides to brake linings and are connected positively to in each case one of the bearing rings via locating pins which are configured separately.

In this way a braking device of modular construction is provided, the holding torque of which is increased, with the same amount of radial installation space, by an odd multiple, depending on the number of disks which are arranged between the armature plate and the pressure plate. Here, the individual disks are configured to be alternately rotating and non-rotating, with the result that a relative movement is produced between them. Said relative movement takes place by way of locating pins which make an axial displacement and rotatory driving possible, the disks being connected alternately to the bearing inner ring and the bearing outer ring.

By accommodating the braking element in one of the bearing rings, normally in the rotating bearing ring, it is in this way possible to achieve compact rolling bearings having a braking device. A further advantage is that by arranging the braking device as an integral rolling bearing component, said device does not have to be additionally connected in a complex manner to the actual bearing arrangement. It is also advantageous that simply by using springs of different dimensions it is possible to influence the magnitude of the pretensioning force and hence the braking force to be applied. Use of the electromagnet also represents a straightforward way of cancelling the braking force, so that in this case the rolling bearing moves freely. Such a rolling bearing of generic type with a braking device can always be used to particular advantage when a constant friction torque is required, but also, under certain circumstances, has to be released very rapidly. This is the case, for example, in the medical field, when the rolling bearing arrangement is used in a rotational connection, for example in a ceiling mount, which is connected to medical appliances of various designs. It is advantageous here that on the one hand the constant friction torque serves to prevent any unwanted turning of the rotational connection, but that on the other hand the rotational connection is easily adjustable by releasing the braking device.

Further advantageous developments of the invention are described in the dependent claims.

According to an embodiment of the invention, the armature plate is held so that it is axially displaceable by multiple, circumferentially spaced locating pins, and is pre-tensioned by multiple, circumferentially spaced spring elements, an air gap being formed between the armature plate and the bearing ring in the absence of any current passing through the coil. In this way the means initiating the braking effect, that is to say the spring elements, and the means cancelling the braking effect, that is to say the coil windings, are arranged directly adjacent in the bearing ring, thereby making maximal use of the overall space available.

According to another embodiment, the pressure plate is intended to be of annular design and to be received via a thread by an associated thread of the bearing ring. This ensures that the air gap of the electromagnet for cancelling the braking force can be adjusted very precisely. If the air gap is set too small, there is a risk that the braking effect will not be cancelled, since the brake lining does not lift off. If the air gap is too large, on the other hand, the magnetic field is weakened and the electromagnet has to he of unnecessarily large design.

According to another embodiment, the rolling bodies are formed by bearing needle rollers of two opposing axial angular contact needle-roller bearings, a point of intersection of their extended axes of rotation lying in the inner bearing ring or in the outer bearing ring. Compared to the known rotational connections, which are preferably embodied as four-point support bearings or cross-roller bearings, the use of two axial angular contact needle-roller bearings makes manufacturing considerably more cost-effective for an equal or higher load rating. In this context it has proved advantageous that the axial angular contact needle-roller bearings are set in an O-arrangement to one another and have runners carrying the raceways. According to a further feature of the invention these runners may then be subjected to a hardening process, it having proved advantageous for the runners and at least one of the bearing rings to be composed of different materials, so that a further reduction in the weight of said bearing arrangement reduction in the weight of said bearing arrangement is feasible. According to another embodiment, the bearing ring without the coil is produced from a light alloy or a plastic, which receives the substantially harder runners of the axial angular contact needle-roller bearings.

According to another additional feature for adjustment of the bearing pre-tension, the bearing ring is of two-part design, the ring being connected to an adjusting nut displaceable in an axial direction. It has proved advantageous here according to a further feature if the adjusting nut is received via a thread by a corresponding mating thread of the bearing ring.

Finally, according to a final feature of the invention, the rolling bearing should lend itself to use in a ceiling mount for medical appliances. Such ceiling mounts have long been known and are described, for example, in DE 36 27 517 A1, DE 43 06 803 A1 and DE 199 63 512 C1. The ceiling mount described in the last prior publication is also provided with a braking device, which comprises two brake rings, which enclose the bearing arrangement radially from the outside.

Here too, the braking device is represented as an additionally produced component, which is to be arranged outside the actual bearing but which again has the disadvantages cited in the state of the art.

Further features of the invention are set forth in the following description and in the drawings, in which exemplary embodiments of the invention are represented in simplified form.

DETAILED DESCRIPTION OF THE DRAWINGS

Figure 3:
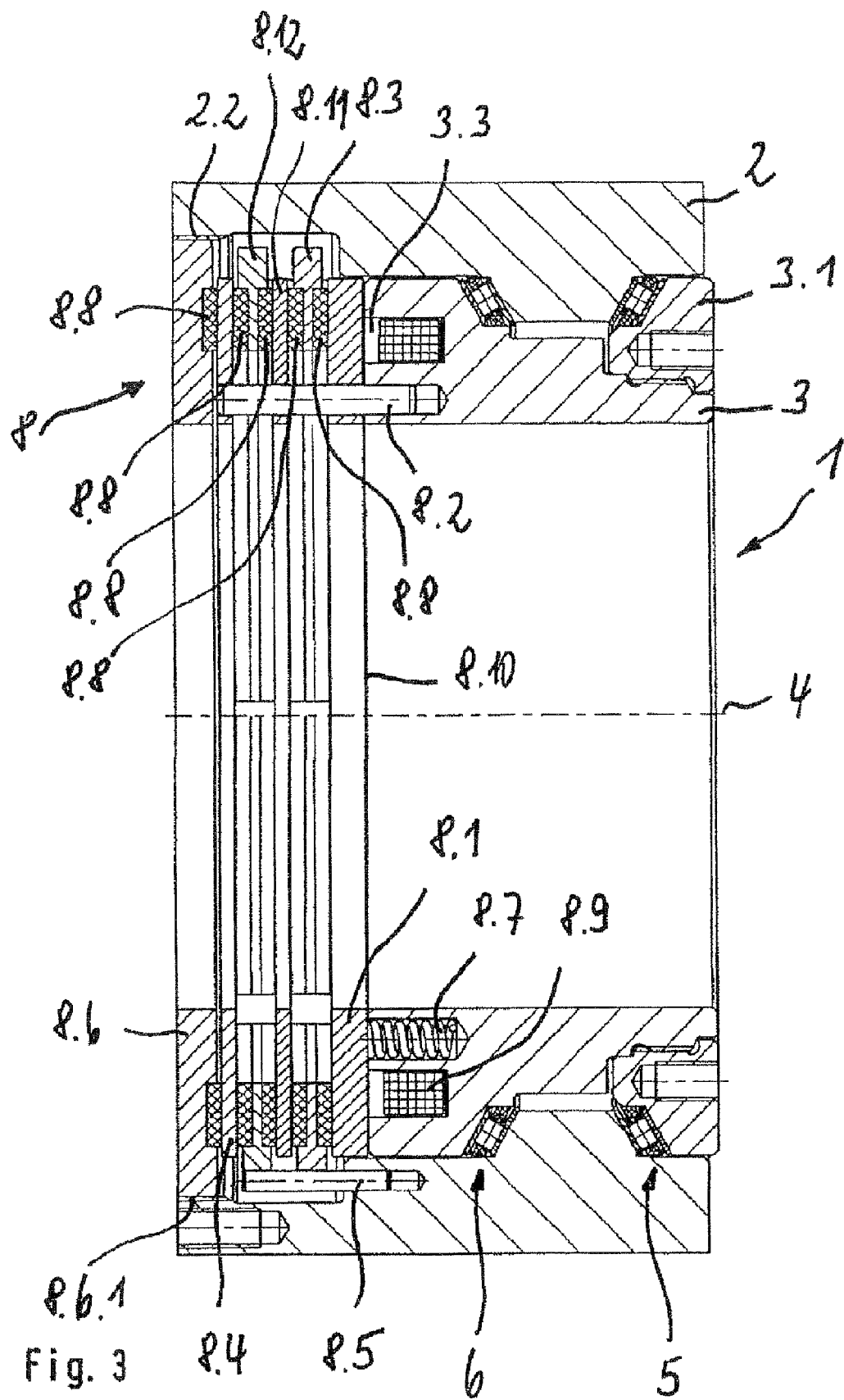
FIG. 3 shows a longitudinal section through a second variant of the invention.
Figure 4:
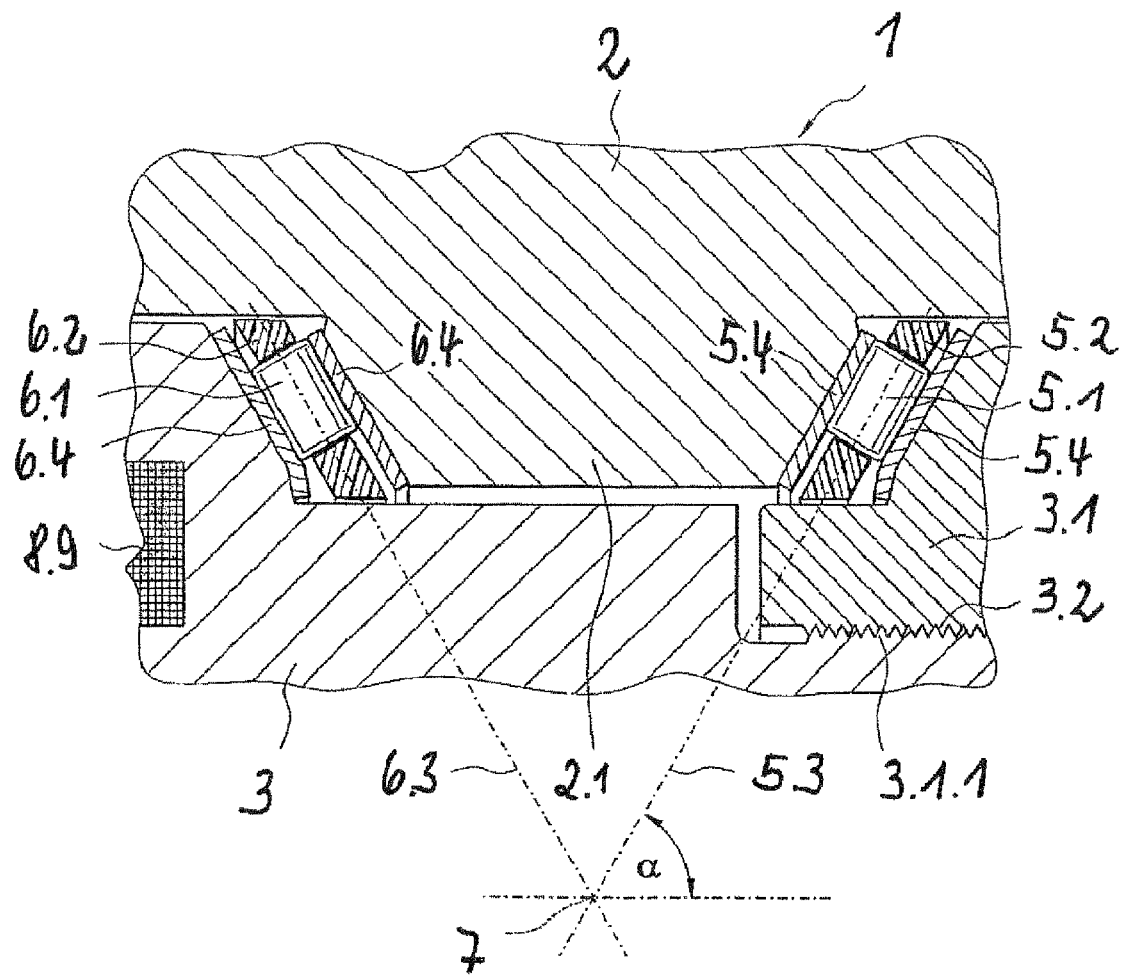
FIG. 4 shows an enlarged section from the bearing in the region of the rolling bodies.

The rolling bearing 1 designed according to the invention and shown in FIGS. 1 to 4 comprises the outer bearing ring 2 and the inner bearing ring 3, which are arranged concentrically one inside the other around the bearing axis 4. Arranged in the annular space formed between them are axial angular contact needle-roller bearings 5, 6, which are set in an O-arrangement to one another. Both have rolling bodies in the form of bearing needle rollers 5.1, 6.1 which are each guided in a cage 5.2, 6.2, the extended axes of rotation 5.3, 6.3 of the bearing needle rollers 5.1, 6.2 intersecting at the point 7, which lies in the inner bearing ring 3. Belonging to each of the axial angular contact needle-roller bearings 5, 6, are two runners 5.4, 6.4, which provide the raceways, not further denoted, for the bearing needle rollers 5.1, 6.1. FIG. 4, in particular, shows that the angle of inclination a may be variable, making it possible to influence the ratio between radial and axial force absorption. As can also be seen, the inner bearing ring 3 is of two-part design, the adjusting nut 3.1 being screwed by its internal thread 3.1.1 onto the external thread 3.2 of the inner bearing ring 3 and thereby being displaceable in an axial direction. In this way, the bearing pre-tension is easily adjustable by tightening the adjusting nut 3.1, the two axial angular contact needle-roller bearings 5, 6 being pressed against the V-shaped projection 2.1 of the outer bearing ring 2.

Figure 1:
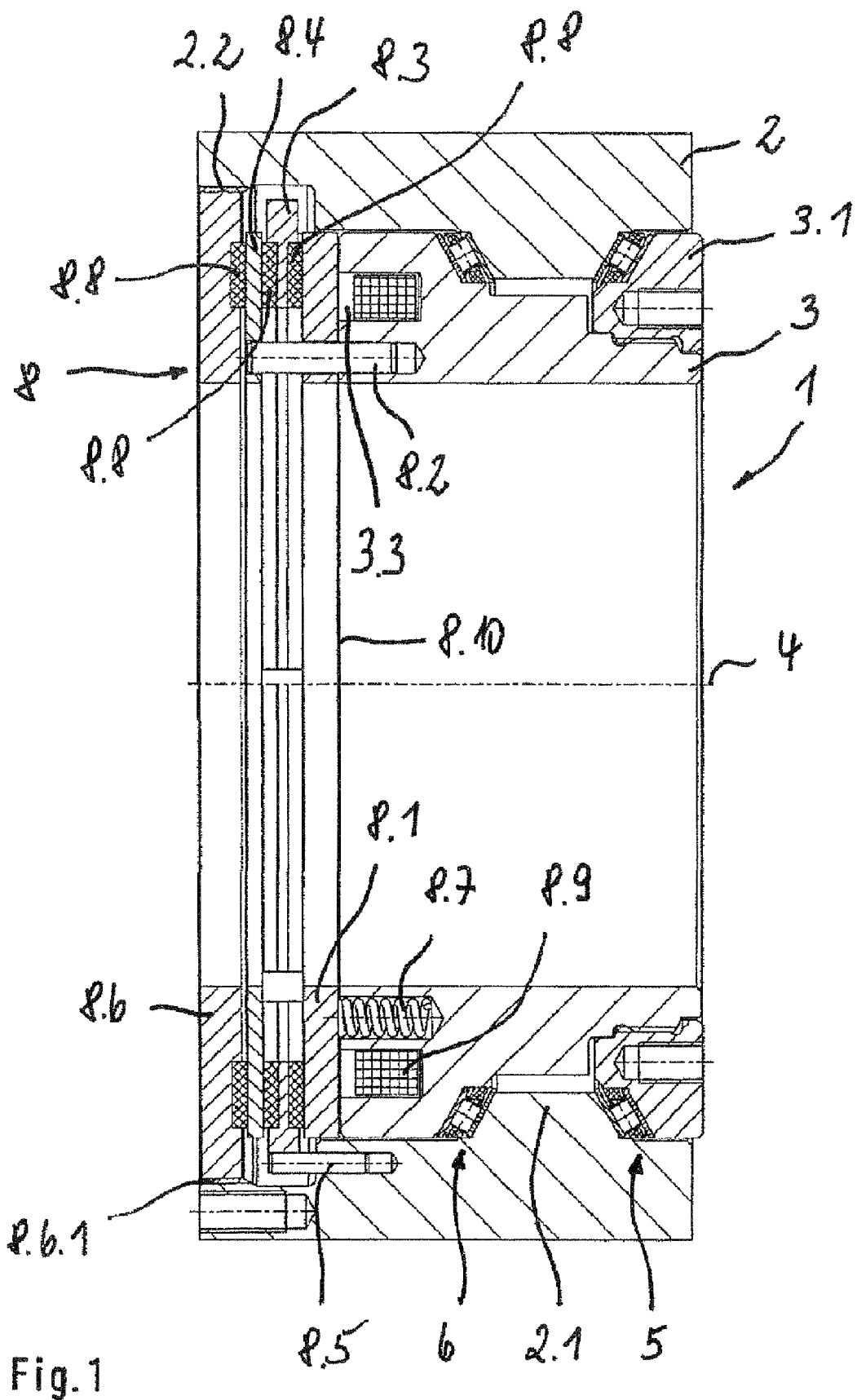
FIG. 1 shows a longitudinal section through a rolling bearing designed according to the invention along the line I-I in FIG. 2.
Figure 2:
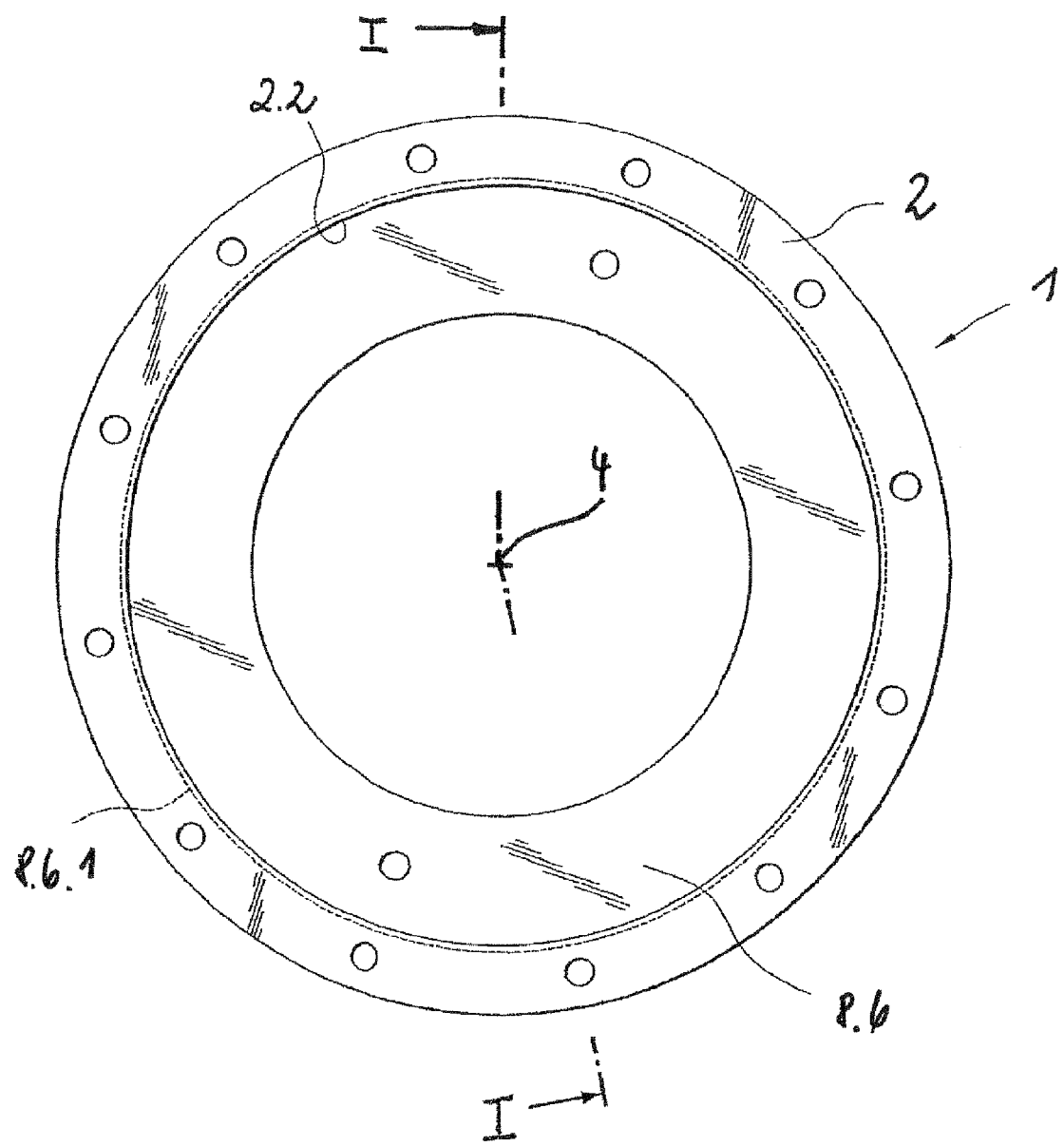
FIG. 2 shows a side view of this bearing.

According to FIG. 1, the braking element 8 according to the invention comprises the ferromagnetic armature plate 8.1, which is of annular design and is connected positively to the rotating bearing inner ring 3 via locating pins 8.2. Furthermore, the locating pins 8.2 are connected to the disk 8.4, with the result that, when the bearing inner ring 3 rotates, the armature plate 8.1 and the disk 8.4 co-rotate with it. The locating pins 8.2 are arranged spaced apart from one another uniformly in the circumferential direction and are dimensioned such that both the armature plate 8.1 and the disk 8.4 are displaceable in the axial direction. A further disk 8.3 which is connected to the stationary bearing outer ring 2 via locating pins 8.5 is arranged between the armature plate 8.1 and the disk 8.4. Furthermore, the pressure plate 8.6 which is screwed via its thread 8.6.1 into the thread 2.2 of the bearing outer ring 2 belongs to the braking element 8. Spring elements 8.7 which are spaced apart from one another uniformly in the circumferential direction and press the armature plate 8.1 in the direction of the pressure plate 8.6 also belong to said braking element 8.

The armature plate 8.1, disks 8.3, 8.4 and pressure plate 8.6 are separated from one another by brake linings 8.8, the arrangement of the friction partners being selected in such a way that they are arranged alternately to be rotating and non-rotating. The armature plate 8.1 and the disk 8.4 co-rotate via the locating pins 8.2 with the bearing inner ring 3, while the pressure plate 8.6 is fixed via its threads 8.6.1 and the disk 8.3 is fixed via the locating pins 8.5 to the bearing outer ring 2. Here, the arrangement of the brake linings 8.8 is carried out in such a way that they are connected fixedly to the disk 8.3 and the pressure plate 8.6.

As can further be seen, the inner bearing ring 3 is provided with the recess 3.3, which is open in an axial direction and in which the coil 8.9 is arranged. In the currentless state of the coil 8.9, the armature plate 8.1 and bearing inner ring 3 are spaced apart from one another by the air gap 8.10 which can be set very accurately by a different axial position of the pressure plate 8.6. In the absence of any current passing through the coil 8.9, the bearing arrangement is braked, that is to say the outer bearing ring 2 and the inner bearing ring 3 are frictionally connected together. The armature plate 8.1, connected to the inner bearing ring 3 by the locating pins 8.2, is thereby pressed by way of the friction lining 8.8 against the disk 8.3, and this in turn by way of the further friction lining 8.8 against the disk 8.4 and this in turn by way of a further brake lining 8.8 against the pressure plate 8.6. With a current passing through the coil 8.9, the magnetic field generated moves the armature plate 8.1 toward the face of the inner bearing ring 3, so that the latter two elements bear tightly against one another and the air gap 8.10 disappears, with the result that the frictional connection between the parts 8.6, 8.4, 8.12, 8.11, 8.3 and 8.1 is canceled.

The second variant of the invention represented in FIG. 3 differs from that shown in FIG. 1 in that the two disks 8.11 and 8.12 are arranged in addition to the disks 8.3 and 8.4, with the result that the braking performance is increased again. The armature plate 8.1 and the disks 8.4 and 8.11 are connected positively to the rotating bearing inner ring 3 via the locating pins 8.2 in such a way that they co-rotate, but are moveable in the axial direction. The stationary bearing outer ring 2 is connected via its thread 2.2 to the thread 8.6.1 of the pressure plate 8.6 and via the locating pins 8.5 to the disks 8.12 and 8.3, with the result that they are likewise fixed, the disks 8.12 and 8.3 being displaceable in the axial direction. The bearing 1 is braked in the currentless state of the coil 8.9, since the armature plate 8.1 and the disks 8.3, 8.11, 8.12, 8.4 are pressed against the pressure plate 8.6 via the spring elements 8.7, all the involved partners being separated from one another by associated brake linings 8.8. When current flows, the coil 8.9 cancels the action of the spring elements 8.7, with the result that the air gap 8.10 is canceled and the frictional connection is canceled by an axial spacing of the involved partners 8.1, 8.3, 8.11, 8.12, 8.4 and 8.6 from one another. Here, the arrangement of the brake linings 8.8 is carried out in such a way that they are connected fixedly to the disks 8.3, 8.12 and the pressure plate 8.6.

REFERENCE NUMERALS

1 Rolling bearing
2 Outer bearing ring
2.1 Projection
2.2 Thread
3 Inner bearing ring
3.1 Adjusting nut
3.1.1 Internal thread
3.2 External thread
3.3 Recess
4 Bearing axis
5 Axial angular contact needle-roller bearing
5.1 Bearing needle roller
5.2 Cage
5.3 Axis of rotation
5.4 Runner
6 Axial angular contact needle-roller bearing
6.1 Bearing needle roller
6.2 Cage
6.3 Axis of rotation
6.4 Runner
7 Point
8 Braking element
8.1 Armature plate
8.2 Locating pin
8.3 Disk
8.4 Disk
8.5 Locating pin
8.6 Pressure plate
8.6.1 Thread
8.7 Spring element
8.8 Brake lining
8.9 Coil
8.10 Air gap
8.11 Disk
8.12 Disk
α Angle of inclination

The invention claimed is:

1. A rolling bearing having a braking device, comprising:
    an outer hearing ring and an inner bearing ring, between which rolling bodies are in rolling motion on associated raceways,
    an electromagnet having one of the bearing rings as soft iron core and a coil which encloses the former,
    a ferromagnetic armature plate connected to the one of the bearing rings, the armature plate being pressed in a direction of a pressure plate connected to the other of the bearing rings to achieve a braking effect, the armature plate being pulled away from said pressure plate in response to actuation of said coil to cancel the braking effect, wherein the pressure plate is of annular design and is received via a thread by an associated thread of the other of the bearing rings, and
    at least one disk is arranged between the armature plate and the pressure plate, the at least one disk being operatively connected on both sides to brake linings and connected for rotation with the one of the bearing rings or the other of the bearing rings via locating pins which are configured separately.

2. The rolling bearing of in claim 1, wherein the armature plate is held so that the armature plate is axially displaceable on the locating pins or on additional locating pins, and multiple, circumferentially spaced spring elements pre-tension the armature plate so that an air gap being formed between the armature plate and the bearing ring in an absence of a current passing through the coil.

3. The rolling hearing of claim 1, wherein the rolling bodies are formed by bearing needle rollers of two opposing axial angular contact needle-roller bearings, a point of intersection of their extended axes of rotation of the bearing needle rollers lying in the inner bearing ring or in the outer bearing ring.

4. The rolling hearing of claim 3, wherein the axial angular contact needle-roller bearings are set in an O-arrangement to one another and have runners carrying the raceways.

5. The rolling bearing of claim 4, wherein the runners have been subjected to a hardening process.

6. The rolling bearing of claim 4, wherein the runners and at least one of the bearing rings are made of different materials.

7. The rolling hearing of claim 6, wherein the other of the bearing rings without the coil is produced front a light alloy or a plastic.

8. The rolling bearing of claim 3, wherein one of the bearing rings for adjustment of the pre-tension is of two-part design, the ring being connected to an adjusting nut displaceable in an axial direction.

9. The rolling bearing of claim 8, wherein the adjusting nut is received via a thread by a corresponding mating thread of the bearing ring.

10. The rolling bearing of claim 1, wherein the rolling bearing can be used in a ceiling mount for medical appliances.

11. The rolling bearing of claim 1, wherein the at least one disk comprises a first disk and a second disk, the first disk being fixed with respect to rotation relative to the pressure plate and disposed between the second disk and the armature plate, the second disk being fixed with respect to rotation relative to the armature plate and disposed between the first disk and the pressure plate.

* * * * *

UNITED STATES PATENT AND TRADEMARK OFFICE
CERTIFICATE OF CORRECTION

PATENT NO. : 8,376,096 B2  
APPLICATION NO. : 12/739452  
DATED : February 19, 2013  
INVENTOR(S) : Nuissl et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 372 days.

Signed and Sealed this
First Day of September, 2015

Michelle K. Lee
*Director of the United States Patent and Trademark Office*